US012761218B2

(12) United States Patent
Zheng et al.

(10) Patent No.: US 12,761,218 B2
(45) Date of Patent: Oct. 13, 2026

(54) MICROFLUIDIC IMMUNOASSAY CHIP AND MICROFLUIDIC LINE IMMUNOASSAY METHOD

(71) Applicant: SHENZHEN YHLO BIOTECH CO., LTD., Shenzhen (CN)

(72) Inventors: Yanping Zheng, Shenzhen (CN); Xiaoyu Cheng, Shenzhen (CN); Daoshun Wei, Shenzhen (CN); Chungen Qian, Shenzhen (CN); Kunhui Hu, Shenzhen (CN)

(73) Assignee: SHENZHEN YHLO BIOTECH CO., LTD, Shenzhen (CN)

( * ) Notice: Subject to any disclaimer, the term of this patent is extended or adjusted under 35 U.S.C. 154(b) by 942 days.

(21) Appl. No.: 18/015,646

(22) PCT Filed: Aug. 20, 2021

(86) PCT No.: PCT/CN2021/113725
§ 371 (c)(1),
(2) Date: Jan. 11, 2023

(87) PCT Pub. No.: WO2022/052787
PCT Pub. Date: Mar. 17, 2022

(65) Prior Publication Data

US 2023/0251250 A1 Aug. 10, 2023

(30) Foreign Application Priority Data

Sep. 8, 2020 (CN) ......................... 202010934760.5

(51) Int. Cl.
*G01N 33/543* (2006.01)
*B01L 3/00* (2006.01)
*G01N 33/58* (2006.01)

(52) U.S. Cl.
CPC ..... *G01N 33/54366* (2013.01); *G01N 33/581* (2013.01)

(58) Field of Classification Search
None
See application file for complete search history.

(56) References Cited

U.S. PATENT DOCUMENTS 8,534,319 B2 9/2013 Bergeron et al.
9,746,413 B2 8/2017 Handique et al.
(Continued)

FOREIGN PATENT DOCUMENTS

CN 101715553 A 5/2010
CN 103998394 A 8/2014
(Continued)

OTHER PUBLICATIONS

Second Chinese Office Action for Chinese Application No. 202010934760.5, mailed Jul. 26, 2025, with English translation, 12 pages.
(Continued)

*Primary Examiner* — Rebecca M Giere
(74) *Attorney, Agent, or Firm* — Kagan Binder, PLLC

(57) ABSTRACT

The present disclosure relates to a microfluidic immunoassay chip and a microfluidic line immunoassay method. The microfluidic immunoassay chip includes a loading cell, a reaction and detection cell, a washing cell, an enzyme storing cell, a substrate cell, and a termination cell, and a waste liquid cell. A detection membrane strip is disposed in the reaction and detection cell and coated with a capture antigen or a capture antibody.

20 Claims, 4 Drawing Sheets

(56) References Cited

U.S. PATENT DOCUMENTS

| | | | | |
|---|---|---|---|---|
| 2009/0253130 | A1* | 10/2009 | Yoo | B01L 3/502723 435/287.2 |
| 2011/0020194 | A1 | 1/2011 | Lee et al. | |
| 2011/0117634 | A1 | 5/2011 | Halamish et al. | |
| 2012/0301867 | A1 | 11/2012 | Kumo et al. | |
| 2014/0134631 | A1 | 5/2014 | Clime et al. | |
| 2017/0333901 | A1 | 11/2017 | Sun et al. | |
| 2018/0304223 | A1 | 10/2018 | Davies et al. | |
| 2018/0371058 | A1* | 12/2018 | Watters | C07K 19/00 |
| 2019/0072547 | A1 | 3/2019 | Ahn et al. | |
| 2023/0251250 | A1 | 8/2023 | Zheng et al. | |

FOREIGN PATENT DOCUMENTS

| | | | | |
|---|---|---|---|---|
| CN | 104293666 | A | 1/2015 | |
| CN | 104502594 | A | 4/2015 | |
| CN | 104694372 | A | 6/2015 | |
| CN | 105316224 | A | 2/2016 | |
| CN | 105498875 | A | 4/2016 | |
| CN | 105562130 | A | 5/2016 | |
| CN | 105618167 | A | 6/2016 | |
| CN | 105785005 | A | 7/2016 | |
| CN | 106076441 | A | 11/2016 | |
| CN | 206292243 | U | 6/2017 | |
| CN | 107338183 | A | 11/2017 | |
| CN | 108535228 | A | 9/2018 | |
| CN | 108823088 | A | 11/2018 | |
| CN | 109012774 | A | 12/2018 | |
| CN | 109212201 | A | 1/2019 | |
| CN | 109395788 | A | 3/2019 | |
| CN | 109499634 | A | 3/2019 | |
| CN | 109517728 | A | 3/2019 | |
| CN | 109884328 | A | 6/2019 | |
| CN | 110045102 | A | 7/2019 | |
| CN | 110093254 | A | 8/2019 | |
| CN | 110260026 | A | 9/2019 | |
| CN | 110713923 | A | 1/2020 | |
| CN | 209974793 | U | 1/2020 | |
| CN | 210510505 | U | 5/2020 | |
| CN | 111330660 | A | 6/2020 | |
| CN | 210787395 | U | 6/2020 | |
| CN | 111454831 | A | 7/2020 | |
| CN | 111957360 | A | 11/2020 | |
| CN | 111965345 | A | 11/2020 | |
| CN | 112275337 | A | 1/2021 | |
| CN | 212410607 | U | 1/2021 | |
| CN | 112808336 | A | 5/2021 | |
| CN | 113019485 | A | 6/2021 | |
| IN | 111965345 | A | 11/2020 | |
| JP | 2011163830 | A | 8/2011 | |
| WO | 2011027832 | A1 | 3/2011 | |
| WO | WO-2018183779 | A1 * | 10/2018 | C12Q 1/6804 |
| WO | 2019040637 | A1 | 2/2019 | |
| WO | 2022048374 | A1 | 3/2022 | |
| WO | 2022052787 | A1 | 3/2022 | |
| WO | 2022170930 | A1 | 8/2022 | |
| WO | 2022206133 | A1 | 10/2022 | |

OTHER PUBLICATIONS

Extended European Search Report for European Application No. 21863442.6, mailed May 24, 2024, (8 pages).

International Search Report, and English Translation thereofe, and Written Opinion for International Application No. PCT/CN2021/110216, mailed Nov. 4, 2021, (17 pages).

International Search Report and Written Opinion, and English Translation therefore, for International Application No. PCT/CN2022/072683, mailed Mar. 24, 2022, (23 pages).

Ruyuan et al., "Design and Fabrication of the Siphon Valve on the Centrifugal Chip," Micronanoelectronic Technology, vol. 51, No. 3, pp. 156-160, Mar. 2014, (5 pages).

International Search Report and Written Opinion, and English Translation thereof, for International Application No. PCT/CN2022/072673, mailed Mar. 23, 2022 (16 pages).

First Chinese Office Action and Search Report for Chinese Application No. 202110337803.6, mailed Jan. 28, 2022, (15 pages).

Second Chinese Office Action for Chinese Application No. 202110337803.6, mailed Jun. 21, 2022, (19 pages).

Qian et al., Unpublished United States 371 U.S. Appl. No. 18/276,587, filed Aug. 9, 2023, (No Copy Enclosed).

Qian et al., Unpublished United States 371 U.S. Appl. No. 18/284,706, filed Sep. 28, 2023, (No Copy Enclosed).

International Search Report, and English Translation thereof, and Written Opinion for International Application No. PCT/CN2021/113725, mailed Nov. 1, 2021, (17 pages).

First Chinese Office Action and English Translation for Chinese Application No. 202010934760.5, mailed Mar. 22, 2025, 12 pages.

Extended European Search Report for European application No. 21865843.3, mailed Jun. 19, 2024, (10 pages).

Lin et al., "Microfluidic Immunoassays," Journal of the Association for Laboratory Automation, Technology Review, vol. 15, Isse. 3, Jun. 1, 2010, (23 pages).

Park et al., "Lab-on-a-Disc for Fully Integrated Multiplex Immunoassays," Analytical Chemistry, vol. 84, pp. 2133-2140, Jan. 25, 2012 (8 pages).

Strohmeier et al., "Centrifugal microfluidic platforms: advanced unit operations and applications," Chem Soc Rev, vol. 44, pp. 6187-6229, 2015, (43 pages).

Tang et al., "A Review of Biomedical Centrifugal Microfluidic Platforms," Micromachines, vol. 7, No. 2, Feb. 2016, (29 pages).

* cited by examiner

MICROFLUIDIC IMMUNOASSAY CHIP AND MICROFLUIDIC LINE IMMUNOASSAY METHOD

CROSS-REFERENCE TO RELATED APPLICATIONS

This application is a national stage for International Application PCT/CN2021/113725, filed on Aug. 20, 2021, entitled "MICROFLUIDIC IMMUNOASSAY CHIP AND MICROFLUIDIC LINE IMMUNOASSAY METHOD" which claims priority to Chinese Patent Application No. 202010934760.5, filed on Sep. 8, 2020 with Chinese patent office, entitled "MICROFLUIDIC IMMUNOASSAY CHIP AND MICROFLUIDIC LINE IMMUNOASSAY METHOD", the content of each application is hereby incorporated by reference in its entirety.

TECHNICAL FIELD

The present disclosure relates to the technical field of microfluidics, and in particular to a microfluidic immunoassay chip and a microfluidic line immunoassay method.

BACKGROUND

Microfluidics, as an emerging science and technology, has been applied to many fields such as chemistry, biology, engineering, physics, etc. Microfluidics is highly interdisciplinary, brings breakthroughs in aspects of temporality, spatiality, and precise manipulation of analysis objects, and can solve many key problems in life analysis. Microfluidics can integrate the detections and experiments that otherwise can only be conducted in laboratories onto a small chip, which not only saves the costs of consumables and time, but more importantly, can integrate multiple detection technologies into a whole, thereby increasing the detection efficiency.

A microfluidic immunochip assay technique is a new micro total analysis and detection method developed in recent years. It combines microfluidics with an immunoassay, building an immunoassay platform on a microfluidic chip, and thus can take advantages of the two assay methods. A very small amount of reagents is needed in the microfluidic assay, which greatly decreases the consumption of expensive immune reagents such as antibodies. Due to the precise manipulation of fluids at micro and nano scales and the highly integrated analytical process, not only the speed of the antigen-antibody reaction is increased and the reaction time is effectively shortened, but also the operating process of the immunoassay is significantly simplified. The unique biological recognition mechanism of the immunoassay further enhances the specificity of the microfluidic assay and renders characteristics such as high sensitivity, high precision, high specificity, etc. to the microfluidic immunoassay chip. Thus, the detection of allergic diseases and autoimmune diseases can be further improved and become more automated and miniaturized by combining the immunoassay with the microfluidic assay.

However, the inner surface of the conventional chip is difficult to be modified and thus difficult to stably and efficiently fix various capture antigens or capture antibodies, which hinders a further wide application of the chip.

SUMMARY

A microfluidic immunoassay chip and a microfluidic line immunoassay method are provided according to various embodiments.

A microfluidic immunoassay chip includes at least one detection unit. The microfluidic immunoassay chip has a rotation center. The detection unit includes:

a loading cell provided with a loading hole;

a reaction and detection cell being in communication with the loading cell, the reaction and detection cell being provided with a detection membrane strip coated with a capture antigen or a capture antibody;

a washing cell configured to be pre-filled with a buffer solution, the washing cell being in communication with the reaction and detection cell;

an enzyme storing cell configured to be pre-filled with an enzyme labelled antibody, the enzyme storing cell being in communication with the reaction and detection cell;

a substrate cell configured to be pre-filled with a reaction substrate for the enzyme labelled antibody, the substrate cell being in communication with the reaction and detection cell;

a termination cell configured to be pre-filled with a reaction terminating liquid, the termination cell being in communication with the reaction and detection cell; and a waste liquid cell configured to receive a waste liquid, the waste liquid cell being in communication with the reaction and detection cell;

wherein the reaction and detection cell is further away from the rotation center than the loading cell, the washing cell, the enzyme storing cell, the substrate cell, and the termination cell, and is closer to the rotation center than the waste liquid cell.

A microfluidic line immunoassay method includes:

providing the above-described microfluidic immunoassay chip;

loading a sample liquid into the loading cell through the loading hole;

centrifuging the microfluidic immunoassay chip, releasing the sample liquid from the loading cell into the reaction and detection cell, and incubating the sample liquid with the detection membrane strip;

releasing the buffer solution from the washing cell into the reaction and detection cell to perform a first washing;

releasing the enzyme labeled antibody from the enzyme storing cell into the reaction and detection cell, and incubating the enzyme labeled antibody with the detection membrane strip;

releasing the buffer solution from the washing cell into the reaction and detection cell to perform a second washing;

releasing the reaction substrate from the substrate cell into the reaction and detection cell, and incubating the reaction substrate with the detection membrane strip;

releasing the buffer solution from the washing cell into the reaction and detection cell to perform a third washing;

releasing the reaction terminating liquid from the termination cell into the reaction and detection cell to terminate the reaction;

detecting a reaction result from the reaction and detection cell.

The above description is only a summary of the technical solutions of the present disclosure. In order to understand the technical means of the present disclosure more clearly and to implement the present disclosure according to the content of the specification, embodiments of the present disclosure will be detailed described as follows in conjunction with the accompanying drawings.

BRIEF DESCRIPTION OF THE DRAWINGS

In order to illustrate the solutions in the embodiments of the present disclosure or in the conventional technology more clearly, the drawings used in the description of the embodiments or the conventional technology will be described briefly as follows. Apparently, the following described drawings are merely some embodiments of the present disclosure, and other drawings can be derived from these drawings by one of ordinary skill in the art without any creative effort.

DETAILED DESCRIPTION

In order to facilitate understanding of the present disclosure, the present disclosure will be comprehensively described and the embodiments of the present disclosure will be provided hereafter. However, the present disclosure can be implemented in many different forms and therefore is not limited to the embodiments described herein. In contrast, the purpose of providing these embodiments is to thoroughly and comprehensively understand the present disclosure.

Unless otherwise defined, all the technical and scientific terms used herein have the same meaning as commonly understood by the person skilled in the art to which the present disclosure belongs. Herein, the terms used in the description of the present disclosure are merely for the purpose of describing specific examples without limiting the present disclosure. The term "and/or" used herein includes any and all combinations of one or more of the associated listed items.

Figure 1:
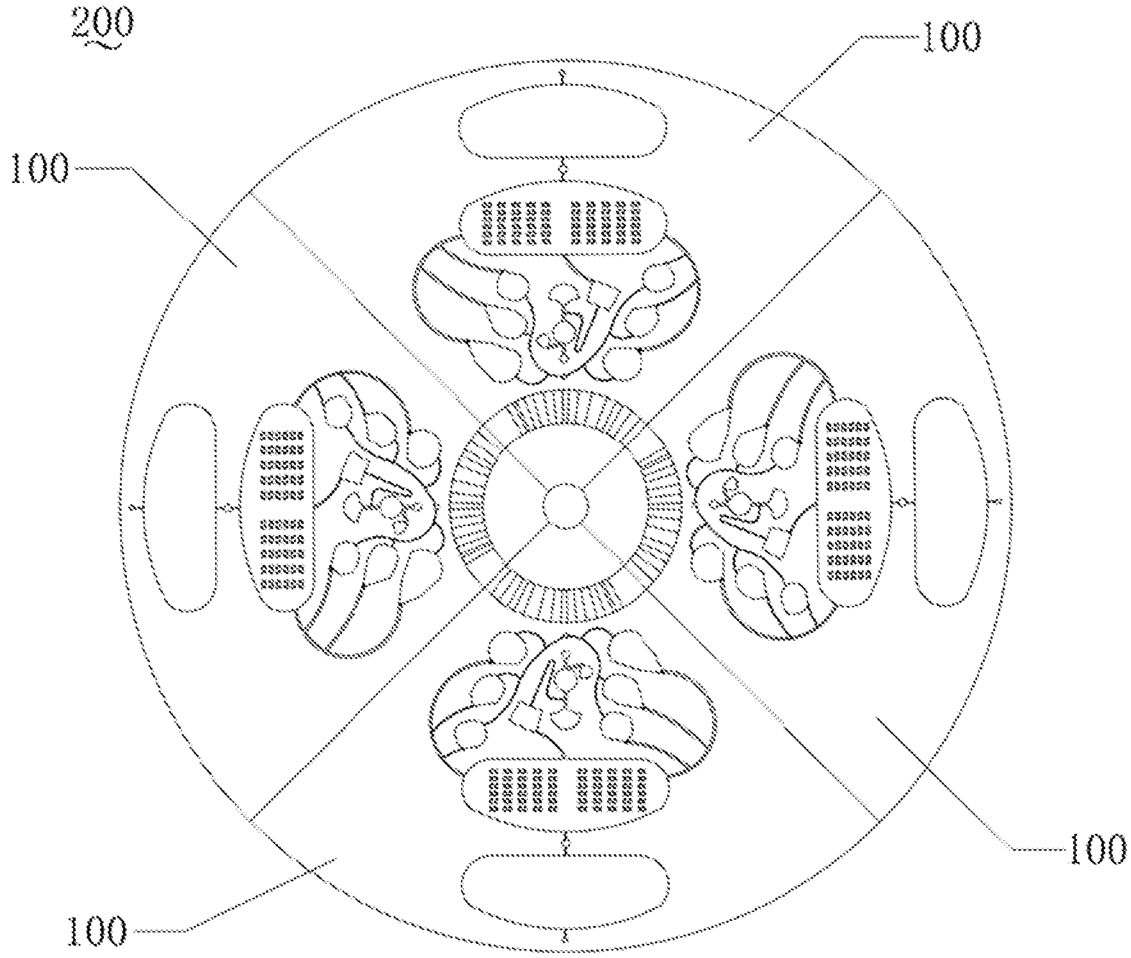
FIG. 1 is a front view of a microfluidic immunoassay chip according to an embodiment.

As shown in FIG. 1, a microfluidic immunoassay chip 200 according to an embodiment of the present disclosure includes a plurality of detection units 100. The microfluidic immunoassay chip 200 is substantially circular in shape and has a rotation center O defined in its central portion. The rotation center O is the center of rotation of the microfluidic immunoassay chip 200 in centrifugal operation.

Figure 2:
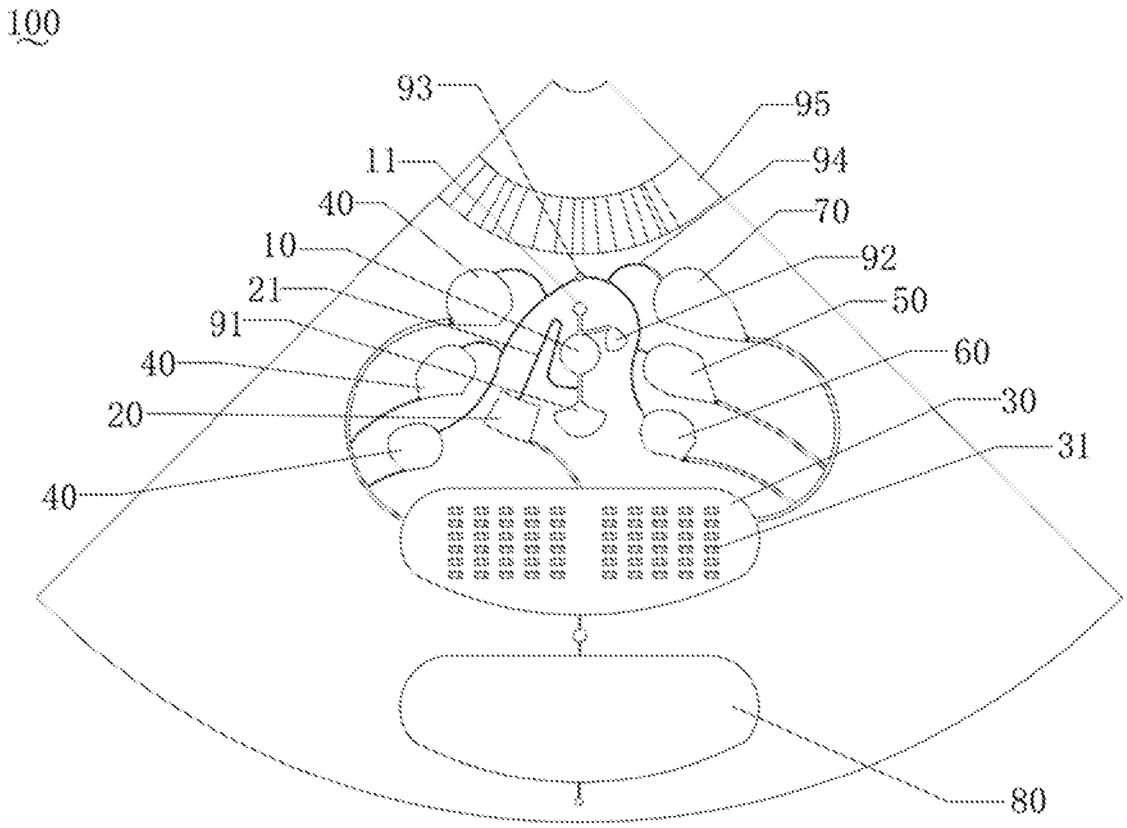
FIG. 2 is a partially enlarged schematic view of a detection unit as shown in FIG. 1.

As shown in FIG. 2, each detection unit 100 includes a loading cell 10, a reaction and detection cell 30, a washing cell 40, an enzyme storing cell 50, a substrate cell 60, a termination cell 70, and a waste liquid cell 80.

The loading cell 10 is provided with a loading hole 11 through which a sample is to be added. The reaction and detection cell 30 is in communication with the loading cell 10. A detection membrane strip 31 is disposed in the reaction and detection cell 30 and coated with a capture antigen or a capture antibody. The washing cell 40 is configured to be pre-filled with a buffer solution and is in communication with the reaction and detection cell 30. The enzyme storing cell 50 is configured to be pre-filled with an enzyme labeled antibody and is in communication with the reaction and detection cell 30. The substrate cell 60 is configured to be pre-filled with a reaction substrate for the above enzyme labeled antibody, and the substrate cell 60 is in communication with the reaction and detection cell 30. The termination cell 70 is configured to be pre-filled with a reaction terminating liquid and is in communication with the reaction and detection cell 30. The waste liquid cell 80 is configured to receive a waste liquid and is in communication with the reaction and detection cell 30.

Figure 3:
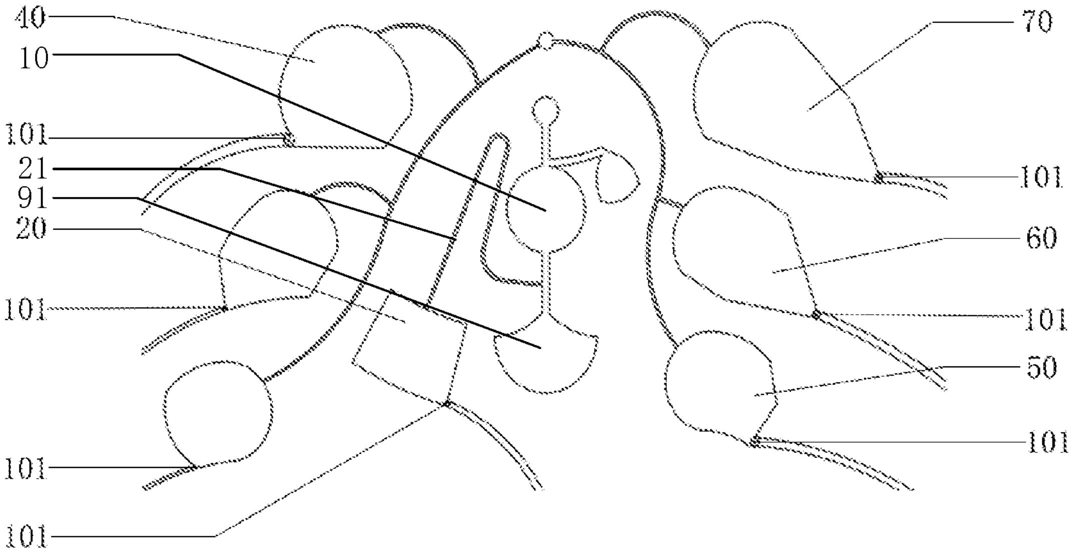
FIG. 3 is a partially enlarged schematic view of the detection unit as shown in FIG. 2.

The reaction and detection cell 30 is further away from the rotation center O than the loading cell 10, the washing cell 40, the enzyme storing cell 50, the substrate cell 60, the termination cell 70, and the waste liquid cell 80. As shown in FIG. 3, a valve 101 is disposed between the reaction and detection cell 30 and each of the loading cell 10, the washing cell 40, the enzyme storing cell 50, the substrate cell 60, the termination cell 70, and the waste liquid cell 80.

In use of the above-described microfluidic immunoassay chip 200, a sample liquid can be loaded into the loading cell 10 through the loading hole 11. Then the microfluidic immunoassay chip 200 is centrifuged to force the sample liquid into the reaction and detection cell 30. The direction and the amplitude of the centrifugation are constantly changed to produce a back and forth mixing and vibration effect on the liquid. In the meanwhile, the capture antigen or the capture antibody on the detection membrane strip 31 captures a target substance in the sample liquid. Thereafter, the liquid is discharged into the waste liquid cell 80 under the action of centrifugation. The buffer solution in the washing cell 40 is released into the reaction and detection cell 30, vibrated back and forth to perform a first washing, and then discharged into the waste liquid cell 80. The enzyme labeled antibody in the enzyme storing cell 50 is released into the reaction and detection cell 30, mixed and incubated, and then discharged into the waste liquid cell 80. The buffer solution in the washing cell 40 is released again to perform a second washing and then discharged into the waste liquid cell 80. The reaction substrate in the substrate cell 60 is released into the reaction and detection cell 30 to achieve a chromogenic reaction and then discharged into the waste liquid cell 80. The buffer solution in the washing cell 40 is released again into the reaction and detection cell 30 to perform a third washing and then discharged into the waste liquid cell 80. Then the reaction terminating liquid in the termination cell 70 is released into the reaction and detection cell 30 to terminate the reaction. After the reaction terminating liquid is evacuated, the reaction result is acquired from the reaction and detection cell 30 and analyzed. The microfluidic immunoassay chip 200 combines the line immunoblotting with the microfluidic assay, utilizes the detection membrane strip 31 disposed in the reaction and detection cell 30 and coated with the capture antigen or the capture antibody as a solid phase detection platform. The microfluidic immunoassay chip 200 requires no modification on the inner surface of the chip, and can stably and efficiently fix various capture antigens or capture antibodies. In addition, the microfluidic immunoassay chip 200 takes advantages of integration and miniaturization of the chip, addresses the shortages of the line immunoblotting using membrane strips such as the complicated and time consumed operation, not only saves the reagents and time, but also requires no specialized personnel to operate, which decreases the detection cost.

It is to be understood that the above-described capture antigen or capture antibody can bind the target substance to be detected in the sample liquid, so that the target substance to be detected is fixed onto the detection membrane strip 31. The enzyme labeled antibody is then bound to the target substance to be detected in the sample liquid, so as to be fixed onto the detection membrane strip 31 and react with the subsequent reaction substrate to develop color change.

In the present embodiment, the detection membrane strip 31 can be made from a membrane strip commonly used in line immunoblotting. The line immunoblotting refers to an assay that transfers antigens or antibodies onto a membrane such as a nitrocellulose membrane as separate bands through electrophoresis due to the differences in molecular mass and structure, which can be used to detect a corresponding antibody in combination with an enzyme labeled antibody and a chromogenic substrate.

In some embodiments, the microfluidic immunoassay chip 200 includes four detection units 100 evenly distributed around the rotation center O to detect four samples simultaneously, which is suitable for various detection samples such as whole blood, plasma, saliva, etc. Of course, in other embodiments, the microfluidic immunoassay chip 200 can be in another shape such as rectangle, polygon, etc. The number of the detection units 100 can be one, two, three, five, seven, etc.

As shown in FIG. 2, in a specific embodiment, the reaction and detection cell 30 is provided with a plurality of detection slots spaced from each other. A plurality of detection membrane strips 31 are correspondingly embedded in the plurality of detection slots. Each of the detection membrane strips 31 is coated with one or more types of capture antigens or capture antibodies thereon. In this way, multiple target substances can be detected at one time, thereby increasing the detection efficiency.

In the present embodiment, the plurality of detection slots are arranged in a rectangular array. In the embodiment as shown in FIG. 1, there are 60 detection slots arranged in 6 rows and 10 columns. It is to be understood that the arrangement manner is not limited thereto and can be adjusted according to needs. In the present embodiment, the detection membrane strips 31 are rectangular membrane strips and the detection slots are rectangular slots. Of course, in other embodiments, the detection membrane strips 31 and the detection slots can be in other shapes such as triangle, circle, etc.

In a specific embodiment, a height difference between a top surface of the detection membrane strip 31 and a top edge of a side wall of the detection slot is 20 μm to 200 μm but is not limited thereto. In this way, the target substance in the sample liquid can be in sufficient contact with the detection membrane strip 31 to have a reaction, which increases the detection efficiency and sensitivity. In the present embodiment, a bottom surface of the detection membrane strip 31 can directly abut against a bottom wall of the detection slot, or there can be a gap between the bottom surface of the detection membrane strip 31 and the bottom wall of the detection slot, so that the target substance in the sample liquid can be in more sufficient contact with the detection membrane strip 31 to have the reaction.

In a specific embodiment, the detection unit 100 further includes a dilution cell 20 configured to be pre-filled with a diluent for diluting the sample. The dilution cell 20 is further away from the rotation center O than the loading cell 10 and is closer to the rotation center O than the reaction and detection cell 30. The dilution cell 20 is in communication with the loading cell 10 through a siphonic channel 21. The reaction and detection cell 30 is in communication with the loading cell 10 through the dilution cell 20. In addition, a valve 101 is further disposed between the reaction and detection cell 30 and the dilution cell 20 to control the release of the liquid from the dilution cell 20. Optionally, the valves 101 are paraffin valves, photosensitive wax valves, or press valves, but are not limited thereto.

As shown in FIG. 3, the siphonic channel 21 from the end thereof being in communication with the loading cell 10 extends in a direction towards the rotation center O, and then bends and extends in a direction away from the rotation center O, thereby being in communication with the dilution cell 20. The bending location is closer to the rotation center O than the loading cell 10. In this way, in centrifugation at a high speed, the siphonic channel 21 is unable to be actuated because the centrifugal force is larger than the capillary force. When the centrifugal force is decreased into a suitable range such that the capillary force is larger than the centrifugal force, the siphonic channel 21 is actuated. At this time, the centrifugal rotation speed can be increased to maintain the siphonic effect, so that a fixed amount of liquid can be forced into the dilution cell 20 due to the siphonic effect, diluted and mixed sufficiently, which is advantageous for improving the detection effect.

As shown in FIG. 3, the detection unit 100 further includes a precipitation cell 91 being in communication with the loading cell 10. The precipitation cell 91 is further away from the rotation center O than the loading cell 10. In this way, after the sample liquid is loaded into the loading cell 10, the sample liquid is stratified by centrifugation and an impurity in the sample liquid is precipitated into the precipitation cell 91 and is thus prevented from subsequently flowing into the reaction and detection cell 30, which is advantageous for increasing the detection efficiency and sensitivity. In an embodiment, the loading cell 10, the precipitation cell 91, the reaction and detection cell 30, and the waste liquid cell 80 are sequentially arranged in a radical direction away from the rotation center O.

In a specific embodiment, the capture antigen is an autoantibody target detection substance or an allergen. Optionally, the autoantibody target detection substance is selected from dsDNA, nucleosome, Ku antigen, histone, ssDNA, SM antigen, ribonucleoprotein (nRNP), ribosomal p protein (RIB-P), anti-mitochondrial antibody M2 (AMA-M2), Jo-1 antigen, desiccation syndrome antigen A (SSA), or desiccation syndrome antigen B (SSB); the allergen is selected from pollen, insect mite, mold, cat hair, dog epithelium, cockroach, house dust, or grass allergens, which are suitable for the inhaled allergen detection and the corresponding autoantibody detection. It is to be understood that the capture antigen or capture antibody coated onto the detection membrane strip 31 is not limited thereto and can be adjusted according to the target substance of the detection.

In a specific embodiment, there are at least three washing cells 40 each being in communication with the reaction and detection cell 30. In this way, the washing with the butter solution can be conveniently performed after each incubation step in the reaction and detection cell 30, which is advantageous for increasing the detection efficiency and sensitivity.

As shown in FIG. 3, the detection unit 100 further includes an excess sample cell 92 being in communication with the loading cell 10. A distance between the excess sample cell 92 and the rotation center O is equal to a distance between the loading cell 10 and the rotation center O, so that the excess sample cell 92 can be used to receive the excess sample liquid. In this way, when the sample liquid is loaded into the loading cell 10 for the centrifugation, the excess sample liquid can flow into the lateral excess sample cell 92 since the excess sample cell 92 and the loading cell 10 are located on the same latitude.

In a specific embodiment, the detection unit 100 further includes a venting hole 93 and a gas channel 94. The washing cell 40, the enzyme storing cell 50, the substrate cell 60, and the termination cell 70 are all in communication with the venting hole 93 through the gas channel 94. The venting hole 93 is closer to the rotation center O than the washing cell 40, the enzyme storing cell 50, the substrate cell 60, and the termination cell 70. The gas channel 94 can have a width of 50 μm to 100 μm and a height of 50 μm to 100 μm, which can balance the gas pressure inside the chip. In an embodiment, the venting hole 93 and the loading hole 11 each are sealed with a hydrophobic and gas-permeable film to prevent the generation of aerosol.

In a specific embodiment, each detection unit 100 is provided with a bar code 95 thereon to distinguish different samples in the detection.

In some embodiments, the processing methods of the microfluidic immunoassay chip 200 include CNC, laser engraving, soft lithography, 3D printing, injection molding, and other methods, but are not limited thereto.

In a specific embodiment, the microfluidic immunoassay chip 200 incudes a bottom plate and a top plate. The loading cell 10, the dilution cell 20, the reaction and detection cell 30, the washing cell 40, the enzyme storing cell 50, the substrate cell 60, and the termination cell 70, the waste liquid cell 80, the precipitation cell 91, and the excess sample cell 92 as described above are all defined in the bottom plate. The loading hole 11, the venting hole 93, and the gas channel 94 are all defined in the top plate. Optionally, the two chambers that are to be in communication with each other or the chamber and the hole that are to be in communication with each other are communicated through a microchannel. For example, the communication between the loading cell 10 and the precipitation cell 91, the communication between the dilution cell 20 and the reaction and detection cell 30, and the communication between the washing cell 40, the enzyme storing cell 50, the substrate cell 60, as well as the termination cell 70 and the venting hole 93, are all achieved by the microchannels.

Figure 4:
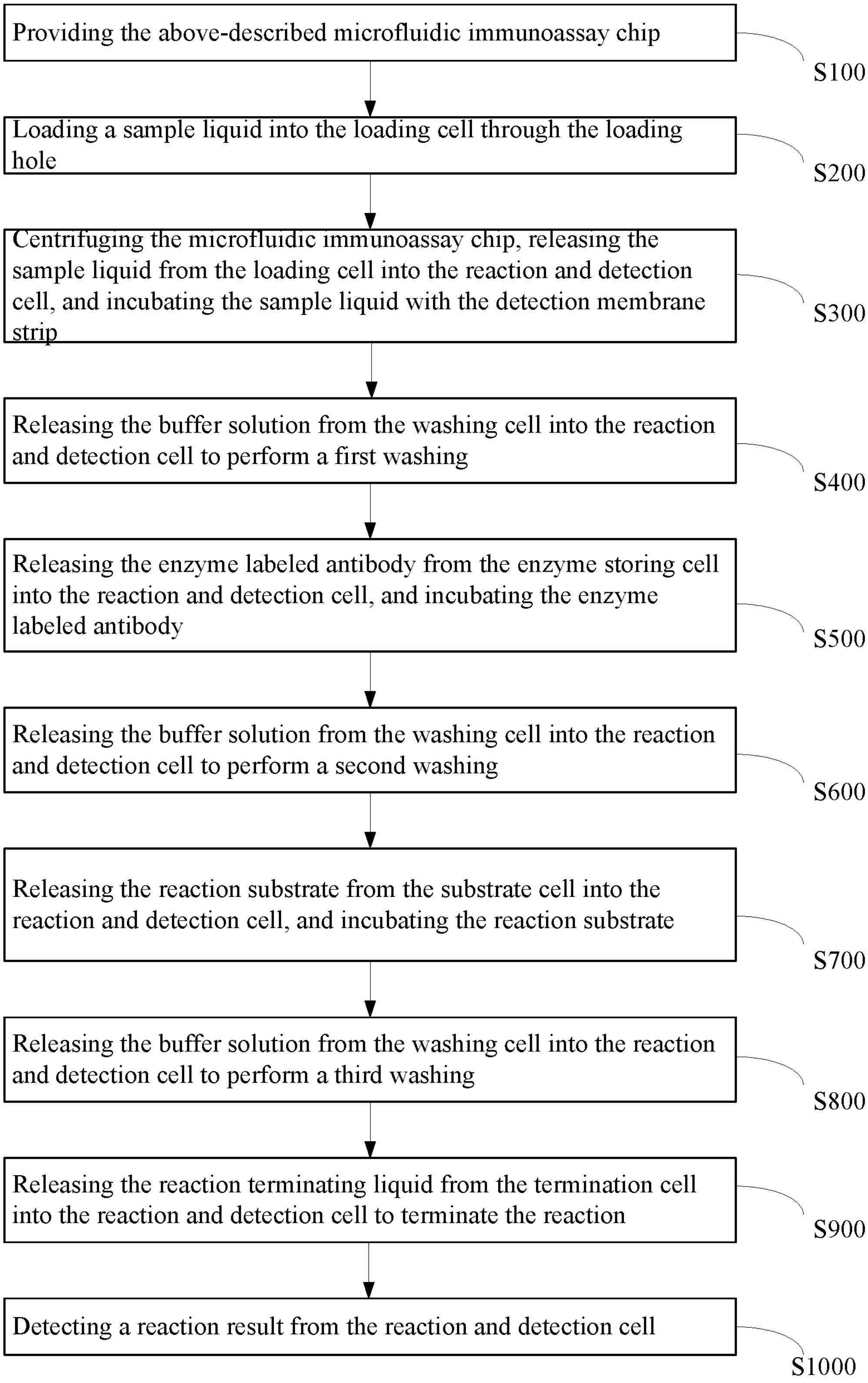
FIG. 4 is a flowchart of a microfluidic line immunoassay method according to an embodiment.

As shown in FIG. 4, a microfluidic line immunoassay method is further disclosed in an embodiment of the present disclosure, including the following steps:

- S100, providing the above-described microfluidic immunoassay chip 200;
- S200, loading a sample liquid into the loading cell 10 through the loading hole 11;
- S300, centrifuging the microfluidic immunoassay chip 200 and opening the valve 101 between the loading cell 10 and the reaction and detection cell 30, so that the sample liquid is released into the reaction and detection cell 30, incubated with the detection membrane strip 31, and then discharged into the waste liquid cell 80;
- S400, opening the valve 101 between the washing cell 40 and the reaction and detection cell 30, so that the buffer solution in the washing cell 40 is released into the reaction and detection cell 30 to perform a first washing and then discharged into the waste liquid cell 80;
- S500, opening the valve 101 between the enzyme storing cell 50 and the reaction and detection cell 30, so that the enzyme labeled antibody in the enzyme storing cell 50 is released into the reaction and detection cell 30, incubated, and then discharged into the waste liquid cell 80;
- S600, opening the valve 101 between the washing cell 40 and the reaction and detection cell 30, so that the buffer solution in the washing cell 40 is released into the reaction and detection cell 30 to perform a second washing and then discharged into the waste liquid cell 80;
- S700, opening the valve 101 between the substrate cell 60 and the reaction and detection cell 30, so that the reaction substrate in the substrate cell 60 is released into the reaction and detection cell 30, incubated, and then discharged into the waste liquid cell 80;
- S800, opening the valve 101 between the washing cell 40 and the reaction and detection cell 30, so that the buffer solution in the washing cell 40 is released into the reaction and detection cell 30 to perform a third washing and then discharged into the waste liquid cell 80;
- S900, opening the valve 101 between the termination cell 70 and the reaction and detection cell 30, so that the reaction terminating liquid is released into the reaction and detection cell 30 to terminate the reaction and then discharged into the waste liquid cell 80;
- S1000, detecting and analyzing the reaction result in the reaction and detection cell 30.

In a specific embodiment, a sample of whole blood is loaded into the loading cell 10 through the loading hole 11. Then the centrifugation is started to separate the plasma components from the whole blood. Then the centrifugal speed is decreased until the siphonic channel 21 is actuated, and then the centrifugal speed is increased and maintained, so that a fixed amount of plasma can be forced into the dilution cell 20 due to the siphonic effect. After the sample enters the dilution cell 20, the centrifugal direction is constantly changed so that the sample is subjected to a vibration and mixing effect. When the sample is mixed uniformly, the valve 101 is opened, allowing the sample solution to enter the reaction and detection cell 30 and to be incubated with the detection membrane strip 30.

The sample liquid after the incubation is discharged into the waste liquid cell 80 under the action of centrifugation at a high speed, before the valve 101 between the washing cell 40 and the reaction and detection cell 30 is opened. As such, the buffer solution in the washing cell 40 is released into the reaction and detection cell 30 to perform the first washing and then discharged into the waste liquid cell 80. The valve 101 between the enzyme storing cell 50 and the reaction and detection cell 30 is opened, so that the enzyme labeled antibody in the enzyme storing cell 50 is released into the reaction and detection cell 30, incubated, and then discharged into the waste liquid cell 80. The valve 101 between the washing cell 40 and the reaction and detection cell 30 is opened, so that the buffer solution in the washing cell 40 is released into the reaction and detection cell 30 to perform a second washing and then discharged into the waste liquid cell 80. The valve 101 between the substrate cell 60 and the reaction and detection cell 30 is opened, so that the reaction substrate in the substrate cell 60 is released into the reaction and detection cell 30, incubated, and then discharged into the waste liquid cell 80. The valve 101 between the washing cell 40 and the reaction and detection cell 30 is opened, so that the buffer solution in the washing cell 40 is released into the reaction and detection cell 30 to perform a third washing and then discharged into the waste liquid cell 80. The valve 101 between the termination cell 70 and the reaction and detection cell 30 is opened, so that the reaction terminating liquid is released into the reaction and detection cell 30 to terminate the reaction and then discharged into the waste liquid cell 80. The reaction result is acquired from the reaction and detection cell 30 and analyzed.

The microfluidic line immunoassay method which adopts the above-described microfluidic immunoassay chip 200 not only can be used to assist the early screening and diagnosis of allergic diseases and autoimmune diseases, but also can be used in the detection of samples from various sources such as the environment and food. In addition, the types of molecules that can be detected are not limited to diseaserelated molecules. In fact, any antigens and antibodies can be detected by this method. Thus, the application of the method is universal.

The microfluidic line immunoassay method combines the line immunoblotting with the microfluidic assay technology, utilizes the detection membrane strip 31 disposed in the reaction and detection cell 30 and coated with the capture antigen or the capture antibody as a solid phase detection platform. The microfluidic immunoassay chip 200 requires no modification on the inner surface of the chip, and can stably and efficiently fix various capture antigens or antibodies. In addition, the microfluidic immunoassay chip 200 takes advantages of integration and miniaturization of the chip, addresses the shortages of the line immunoblotting using membrane strips such as the complicated and time consumed operation, not only saves the reagents and time, but also requires no specialized personnel to operate, which decreases the detection cost.

The technical features of the above-described embodiments can be combined arbitrarily. To simplify the description, not all possible combinations of the technical features in the above embodiments are described. However, all of the combinations of these technical features should be considered as being fallen within the scope of the present disclosure, as long as such combinations do not contradict with each other.

The foregoing embodiments merely illustrate some embodiments of the present disclosure, and descriptions thereof are relatively specific and detailed. However, it should not be understood as a limitation to the patent scope of the present disclosure. It should be noted that, a person of ordinary skill in the art may further make some variations and improvements without departing from the concept of the present disclosure, and the variations and improvements falls in the protection scope of the present disclosure. Therefore, the protection scope of the present disclosure shall be subject to the appended claims. The technical features of the above-described embodiments can be combined arbitrarily. To simplify the description, not all possible combinations of the technical features in the above embodiments are described. However, all of the combinations of these technical features should be considered as being fallen within the scope of the present disclosure, as long as such combinations do not contradict with each other.

What is claimed is:

1. A microfluidic immunoassay chip, comprising at least one detection unit and having a rotation center, wherein the detection unit comprises:

a loading cell provided with a loading hole;

a reaction and detection cell being in communication with the loading cell, the reaction and detection cell being provided with a detection membrane strip coated with a capture antigen or a capture antibody;

a washing cell configured to be pre-filled with a buffer solution, the washing cell being in communication with the reaction and detection cell;

an enzyme storing cell configured to be pre-filled with an enzyme labelled antibody, the enzyme storing cell being in communication with the reaction and detection cell;

a substrate cell configured to be pre-filled with a reaction substrate for the enzyme labelled antibody, the substrate cell being in communication with the reaction and detection cell;

a termination cell configured to be pre-filled with a reaction terminating liquid, the termination cell being in communication with the reaction and detection cell, the reaction and detection cell being configured to receive the reaction terminating liquid released from the termination cell; and a waste liquid cell configured to receive a waste liquid discharged from the reaction and detection cell, the waste liquid cell being in communication with the reaction and detection cell;

wherein the reaction and detection cell is further away from the rotation center than the loading cell, the washing cell, the enzyme storing cell, the substrate cell, and the termination cell, and is closer to the rotation center than the waste liquid cell.

2. The microfluidic immunoassay chip of claim 1, further comprising a valve disposed between the reaction and detection cell and each of the loading cell, the washing cell, the enzyme storing cell, the substrate cell, and the termination cell.

3. The microfluidic immunoassay chip of claim 1, wherein the reaction and detection cell comprises a plurality of detection slots spaced from each other, and the detection membrane strip is a plurality of detection membrane strips embedded in the plurality of detection slots in a one-to-one correspondence.

4. The microfluidic immunoassay chip of claim 3, wherein a height difference between a top surface of each detection membrane strip and a top edge of a side wall of a corresponding detection slot is about 20 μm to about 200 μm.

5. The microfluidic immunoassay chip of claim 1, wherein the detection unit further comprises a dilution cell configured to be pre-filled with a diluent; the dilution cell is further away from the rotation center than the loading cell and closer to the rotation center than the reaction and detection cell; the dilution cell is in communication with the loading cell through a siphonic channel; and the reaction and detection cell is in communication with the loading cell through the dilution cell.

6. The microfluidic immunoassay chip of claim 5, wherein the siphonic channel from one end thereof being in communication with the loading cell extends in a direction towards the rotation center, bends at a position closer to the rotation center than the loading cell, and extends in a direction away from the rotation center, thereby being in communication with the dilution cell.

7. The microfluidic immunoassay chip of claim 1, wherein the detection unit further comprises a precipitation cell being in communication with the loading cell, and the precipitation cell is further away from the rotation center than the loading cell.

8. The microfluidic immunoassay chip of claim 1, wherein the capture antigen is an autoantibody target detection substance or an allergen.

9. The microfluidic immunoassay chip of claim 8, wherein the autoantibody target detection substance is selected from dsDNA, nucleosome, Ku antigen, histone, ssDNA, SM antigen, nRNP, RIB-P, AMA-M2, Jo-1 antigen, SSA, or SSB.

10. The microfluidic immunoassay chip of claim 8, wherein the allergen is selected from pollen, mite, mold, cat hair, dog epithelium, cockroach, house dust, or grass allergens.

11. The microfluidic immunoassay chip of claim 1, wherein the washing cell is at least three washing cells each being in communication with the reaction and detection cell.

12. The microfluidic immunoassay chip of claim 1, wherein the detection unit further comprises an excess sample cell being in communication with the loading cell, and a distance between the excess sample cell and the rotation center is equal to a distance between the loading cell and the rotation center.

13. The microfluidic immunoassay chip of claim 1, wherein the detection unit further comprises a venting hole and a gas channel, the venting hole is closer to the rotation center than the washing cell, the enzyme storing cell, the substrate cell, and the termination cell; the washing cell, the enzyme storing cell, the substrate cell, and the termination cell each are in communication with the venting hole through the gas channel.

14. The microfluidic immunoassay chip of claim 13, wherein a width of the gas channel is about 50 μm to about 100 μm, and a height of the gas channel is about 50 μm to about 100 μm.

15. The microfluidic immunoassay chip of claim 13, further comprising a bar code disposed on the detection unit.

16. A microfluidic line immunoassay method, comprising:

providing the microfluidic immunoassay chip of claim 1;

loading a sample liquid into the loading cell through the loading hole;

centrifuging the microfluidic immunoassay chip, releasing the sample liquid from the loading cell into the reaction and detection cell, and incubating the sample liquid with the detection membrane strip;

releasing the buffer solution from the washing cell into the reaction and detection cell to perform a first washing;

releasing the enzyme labeled antibody from the enzyme storing cell into the reaction and detection cell, and incubating the enzyme labeled antibody with the detection membrane strip;

releasing the buffer solution from the washing cell into the reaction and detection cell to perform a second washing;

releasing the reaction substrate from the substrate cell into the reaction and detection cell, and incubating the reaction substrate with the detection membrane strip;

releasing the buffer solution from the washing cell into the reaction and detection cell to perform a third washing;

releasing the reaction terminating liquid from the termination cell into the reaction and detection cell to terminate the reaction;

detecting a reaction result from the reaction and detection cell.

17. The method of claim 16, wherein in the releasing the sample liquid from the loading cell into the reaction and detection cell, the sample liquid is released from the loading cell into a dilution cell and diluted, and then the diluted sample liquid is released from the dilution cell into the reaction and detection cell.

18. The method of claim 16, wherein in the releasing the sample liquid from the loading cell into the reaction and detection cell, the sample liquid is stratified by centrifugation and an impurity in the sample liquid is precipitated into a precipitation cell, and the sample liquid after the precipitation is released from the loading cell into the reaction and detection cell.

19. The method of claim 16, wherein in the releasing the sample liquid from the loading cell into the reaction and detection cell, excess sample liquid is forced into an excess sample cell.

20. A microfluidic immunoassay chip, comprising at least one detection unit and having a rotation center, wherein the detection unit comprises:

a loading cell provided with a loading hole;

a reaction and detection cell being in communication with the loading cell, the reaction and detection cell being provided with a detection membrane strip coated with a capture antigen or a capture antibody;

a washing cell configured to be pre-filled with a buffer solution, the washing cell being in communication with the reaction and detection cell, the reaction and detection cell being configured to receive the buffer solution released from the washing cell;

an enzyme storing cell configured to be pre-filled with an enzyme labelled antibody, the enzyme storing cell being in communication with the reaction and detection cell;

a substrate cell configured to be pre-filled with a reaction substrate for the enzyme labelled antibody, the substrate cell being in communication with the reaction and detection cell;

a termination cell configured to be pre-filled with a reaction terminating liquid, the termination cell being in communication with the reaction and detection cell, the reaction and detection cell being configured to receive the reaction terminating liquid released from the termination cell; and a waste liquid cell configured to receive a waste liquid discharged from the reaction and detection cell, the waste liquid cell being in communication with the reaction and detection cell; wherein a side of the reaction and detection cell adjacent to the rotation center is further away from the rotation center than the loading cell, the washing cell, the enzyme storing cell, the substrate cell, and the termination cell, and a side of the reaction and detection cell away from the rotation center is closer to the rotation center than the waste liquid cell.

* * * * *